(12) United States Patent
DiDomenico et al.

(10) Patent No.: US 6,744,516 B2
(45) Date of Patent: Jun. 1, 2004

(54) OPTICAL PATH STRUCTURE FOR OPEN PATH EMISSIONS SENSING

(75) Inventors: John DiDomenico, Tucson, AZ (US); Robert A. Gentala, Tucson, AZ (US); Craig S. Rendahl, Tuscon, AZ (US)

(73) Assignee: SPX Corporation, Charlotte, NC (US)

( * ) Notice: Subject to any disclaimer, the term of this patent is extended or adjusted under 35 U.S.C. 154(b) by 322 days.

(21) Appl. No.: 09/934,272

(22) Filed: Aug. 21, 2001

(65) Prior Publication Data

US 2003/0043378 A1 Mar. 6, 2003

(51) Int. Cl.$^7$ .............................. G01N 21/00; G01J 5/02
(52) U.S. Cl. .................... 356/437; 356/438; 250/338.5; 250/339.13; 73/1.06
(58) Field of Search ................... 250/338.5, 339.13; 356/437, 438; 73/1.02, 1.06, 23.3

(56) References Cited

U.S. PATENT DOCUMENTS

| | | | | |
|---|---|---|---|---|
| 3,696,247 A | | 10/1972 | McIntosh et al. ....... | 250/83.3 H |
| 3,811,776 A | | 5/1974 | Blau, Jr. ...................... | 356/51 |
| 3,904,880 A | * | 9/1975 | Benz et al. ................. | 250/343 |
| 3,957,372 A | | 5/1976 | Jowett et al. ................ | 356/51 |
| 3,958,122 A | | 5/1976 | Jowett et al. ............... | 250/346 |
| 3,973,848 A | | 8/1976 | Jowett et al. ................ | 356/51 |
| 4,012,144 A | | 3/1977 | Hedelman .................... | 356/73 |
| 4,013,260 A | | 3/1977 | McClatchie et al. ........ | 250/343 |
| 4,160,373 A | | 7/1979 | Fastaia et al. ................ | 73/23 |
| 4,171,909 A | | 10/1979 | Kramer et al. ................ | 356/73 |
| 4,204,768 A | | 5/1980 | N'Guyen .................... | 356/243 |
| 4,310,249 A | | 1/1982 | Kramer ....................... | 356/414 |
| 4,348,732 A | | 9/1982 | Kreft .......................... | 364/571 |
| 4,372,155 A | | 2/1983 | Butler et al. ................. | 73/114 |
| 4,390,785 A | | 6/1983 | Faulhaber et al. .......... | 250/330 |

(List continued on next page.)

OTHER PUBLICATIONS

Bureau of Automotive Repair; "On Road Emissions Measurement System (OREMS) Specifications"; OREMS Specifications–Version o, Jan. 28, 2002; 2002 California DCA/BAR.

Jimenez–Palacios, José Luis; "Understanding and Quantifying Motor Vehicle Emissions with Vehicle Specific Power and TILDAS Remote Sensing"; Massachusetts Institute of Technology, Feb. 1999.

Radian Corp.; "Developing an Inspection/Maintenance Program for Alternatively–Fueled Vehicles"; 1993.

Islam, Muhammed, Rendahl, Craig S., CORS, Rebecca; "Wisconsin's Remove Vehicle Emissions Sensing Study"; Final Report 1995.

Walsh, P.A., Gertler, A.W.; "Texas 1996 Remote Sensing Feasibility Study"; Final Report 1997.

Popp, Peter J.; "Development of a High–Speed Ultraviolet Spectrophotometer Capable of Real–Time NO and Aromatic Hydrocarbon Detection in Vehicle Exhaust"; pp. 4–3 & 4–12;Coordinating Research Council 1997.

McVey, Iain Frederick; "Development of a Remote Sensor for Mobile Source Nitric Oxide"; University of Denver 1992.

Beaton, S.P., Bishop, G.A. and Stedman D.H.; Emissions Characteristics of Mexico City Vehicles; pp. 42, 1424–1429; Journal of Air and Waste Management Assoc. 1992.

(List continued on next page.)

*Primary Examiner*—Russell Adams
*Assistant Examiner*—Magda Cruz
(74) *Attorney, Agent, or Firm*—Baker & Hostetler LLP (57) ABSTRACT

A gas component analysis system transmits, reflects, and detects light using infrared light source; a reflector unit; and a light detector. The light is transmitted through a gas, such as air containing vehicle emissions, reflected, and detected for analysis and measurement of the amount of absorption that has occurred at known wavelengths. The amount of absorption may be used to determine concentrations of reference gases corresponding to specific wavelengths.

17 Claims, 6 Drawing Sheets

U.S. PATENT DOCUMENTS

| | | | | |
|---|---|---|---|---|
| 4,432,316 | A | 2/1984 | Ogita | 123/328 |
| 4,490,845 | A | 12/1984 | Steinbruegge et al. | 382/1 |
| 4,560,873 | A | 12/1985 | McGowan et al. | 250/339 |
| 4,602,160 | A | 7/1986 | Mactaggart | 250/341 |
| 4,632,563 | A | 12/1986 | Lord, III | 356/437 |
| 4,638,345 | A | 1/1987 | Elabd et al. | 357/24 |
| 4,663,522 | A | 5/1987 | Welbourn et al. | 250/223 R |
| 4,678,914 | A | 7/1987 | Melrose et al. | 250/343 |
| 4,687,934 | A | 8/1987 | Passaro et al. | 250/343 |
| 4,710,630 | A | 12/1987 | Kuppenheimer, Jr. et al. | 250/353 |
| 4,746,218 | A | 5/1988 | Lord, III | 356/437 |
| 4,795,253 | A | 1/1989 | Sandridge et al. | 356/51 |
| 4,818,705 | A | 4/1989 | Schneider et al. | 436/164 |
| 4,829,183 | A | 5/1989 | McClatchie et al. | 250/346 |
| 4,868,622 | A | 9/1989 | Shigenaka | 357/30 |
| 4,875,084 | A | 10/1989 | Tohyama | 357/30 |
| 4,914,719 | A | 4/1990 | Conlon et al. | 250/339 |
| 4,924,095 | A | 5/1990 | Swanson, Jr. | 250/338.5 |
| 4,963,023 | A | 10/1990 | Goldovsky et al. | 356/308 |
| 4,999,498 | A | 3/1991 | Hunt et al. | 250/338.5 |
| 5,002,391 | A | 3/1991 | Wolfrum et al. | 356/307 |
| 5,041,723 | A | 8/1991 | Ishida et al. | 250/339 |
| 5,061,854 | A | 10/1991 | Kroutil et al. | 250/339 |
| 5,076,699 | A | 12/1991 | Ryan et al. | 356/437 |
| 5,157,288 | A | 10/1992 | Hill | 307/511 |
| 5,185,648 | A | 2/1993 | Baker et al. | 257/189 |
| 5,210,702 | A | 5/1993 | Bishop et al. | 364/496 |
| 5,239,860 | A | 8/1993 | Harris et al. | 73/61.48 |
| 5,252,828 | A | 10/1993 | Kert et al. | 250/339 |
| 5,255,511 | A | 10/1993 | Maus et al. | 60/274 |
| 5,268,745 | A * | 12/1993 | Goody | 356/418 |
| 5,307,626 | A | 5/1994 | Maus et al. | 60/274 |
| 5,319,199 | A | 6/1994 | Stedman et al. | 250/338.5 |
| 5,332,901 | A | 7/1994 | Eckles et al. | 250/345 |
| 5,343,043 | A * | 8/1994 | Johnson | 250/338.5 |
| 5,361,171 | A | 11/1994 | Bleier | 359/855 |
| 5,371,367 | A | 12/1994 | DiDomenico et al. | 250/338.5 |
| 5,373,160 | A | 12/1994 | Taylor | 250/338.5 |
| 5,401,967 | A * | 3/1995 | Stedman et al. | 250/338.5 |
| 5,418,366 | A | 5/1995 | Rubin et al. | 250/338.5 |
| 5,489,777 | A | 2/1996 | Stedman et al. | 250/338.5 |
| 5,498,872 | A | 3/1996 | Stedman et al. | 250/338.5 |
| 5,545,897 | A | 8/1996 | Jack | 250/339.13 |
| 5,583,765 | A | 12/1996 | Kleehammer | 364/423.098 |
| 5,591,975 | A | 1/1997 | Jack et al. | 250/338.5 |
| 5,621,166 | A | 4/1997 | Butler | 73/116 |
| 5,644,133 | A | 7/1997 | Didomenico et al. | 250/338.5 |
| 5,719,396 | A | 2/1998 | Jack et al. | 250/338.5 |
| 5,726,450 | A | 3/1998 | Peterson et al. | 250/338.5 |
| 5,739,535 | A * | 4/1998 | Koch et al. | 250/339.13 |
| 5,797,682 | A | 8/1998 | Kert et al. | 374/123 |
| 5,812,249 | A | 9/1998 | Johnson et al. | 356/28 |
| 5,831,267 | A | 11/1998 | Jack et al. | 250/338.5 |
| 5,922,948 | A | 7/1999 | Lesko et al. | 73/117.3 |
| 6,057,923 | A | 5/2000 | Sachse | 356/364 |
| 6,230,087 | B1 | 5/2001 | Didomenico et al. | 701/29 |
| 6,275,290 | B1 * | 8/2001 | Cerni et al. | 356/335 |
| 6,307,201 | B1 | 10/2001 | Didomenico et al. | 250/339.13 |
| 6,455,851 | B1 * | 9/2002 | Lord et al. | 250/338.5 |
| 2003/0057373 | A1 * | 3/2003 | DiDomenico et al. | 250/338.5 |
| 2003/0057383 | A1 * | 3/2003 | DiDomenico et al. | 250/504 R |
| 2003/0063283 | A1 * | 4/2003 | DiDomenico et al. | 356/437 |

OTHER PUBLICATIONS

Zhang, Yi, Stedman, Donald H., Bishop, Gary A., Beaton, Stuart P., Guenther, Paul L. and McVey, Iain F.; "Enhancement of Remote Sensing for Mobile Source Nitric Oxide"; Journal of Air & Waste Management 1996; vol. 46, pp. 25–29.

Popp, Peter John; "Remote Sensing of Nitric Oxide Emissions from Planes, Trains and Automobiles"; University of Denver 1999.

Zhang, Yi, Stedman, Donald H., Bishop, Gary A., Beaton, Stuart P., and Guenther, Paul L.; "Worldwide On–Road Vehicle Exhaust Emissions Study by Remote Sensing"; Environmental Science & Technology 1995;vol. 29#9. pp. 2286–2294.

Glover, Edward L. , Mickelsen, Jan and McClement Dennis; Evaluation of Methods to Determine Catalyst Efficiency in the Inspection/Maintenance Process; Society of Automotive Engineers; SAE#9600092.

Butler, James, Gierczak, Christine and Liscombe Paula; "Factors Affecting the NDIR Measurement of Exhaust Hydrocarbons"; Coordinating Research Council 1995; pp. 4–171 & 4–190.

MacKay, Gervase I., Nadler, S. Don, Karecki, David R., Schiff, Harold I., Butler, James W., Gierczak, Christine A. and Jesion, Gerald; "Final Phase 1b Report to the CRC and NREL for Research Performed Under Agreement No. VE–8–2"; Coordinating Research Council 1994.

Peterson, James E. and Stedman, Donald H.; "Find and Fix the Polluters"; Chemtech 1992; pp. 47–53.

Bishop, Gary A. and Stedman Donald H.; "Infrared Emissions and Remote Sensing"; Journal of Air and Waste Management Assoc. 1992; vol. 42#5, pp. 695–697.

Bishop, Gary A., Starkey, John R., Ihlenfeldt, Anne, Williams, Walter J. and Stedman Donald H.; "IR Long–Path Photometry: A Remote Sensing Tool for Automobile Emissions"; Analytical Chemistry 1989; vol. 61#10, pp. 671A–677A Axelsson, Hakan, Eilard, Anders, Emanuelsson, Annika, Galle, Bo, Edner, Hans, Regnarson Par and Kloo Henrik; "Measurement of Aromatic Hydrocarbons with the DOAS Technique"; Applied Spectroscopy 1995; vol. 49#9, pp. 1254–1260.

Baum, Marc M., Kiyomiya, Eileen S., Kumar Sasi and Lappas, Anastasios M. '"Multicomponent Remote Sensing of Vehicle Exhaust by Dispersive Absorption Spectroscopy. 1. Effect of Fuel Type and Catalyst Performance"; Environmental Science and Technology 2000; pp. 34 & 2851–2858.

Stedman, Donald H. and Smith, Dennis L.; "$NO_x$ Data by Remote Sensing"; Coordinating Research Council 1995; pp. 4–47 & 4–63.

Shore, P.R. and Devries, R.S.; "On–line Hydrocarbon Speciation Using FTIR and CI–MS"; Society of Automotive Engineers 1992; SAE #922246.

Bishop, Gary A. and Stedman, Donald H.; "On–Road Carbon Monoxide Emission Measurement Comparisons for the 1988–1989 Colorado Oxy–Fuels Program"; Environmental Science & Technology 1990; pp. 24 & 843–847.

Stedman, Donald H., Bishop, Gary, Peterson, James E., and Geunther, Paul L.; "On–Road CO Remote Sensing in the Los Angeles Basin"; CA–EPA (CARB) 1991; pp. 24 & 843–847.

X–Rite Incorporated; "A Guide to Integrating Sphere Theory and Applications"; 2002; www.labsphere.com.

Geunther, Paul L., Stedman, Donald H., Bishop, Gary A., Beaton, Stuaret P., Bean, James H. and Quine Richard W.; "A Hydrocarbon Detector for the Remote Sensing of Vehicle Exhaust Emissions"; Review of Scientific Instruments 1994; vol. 66(4), pp. 3024–3029.

Stephens, Robert D., Mulawa, Patricia A., Giles, Michael T., Kennedy, Kenneth G., Groblicki, Peter J. and Cadle, Steven H.; "An Experimental Evaluation of Remote Sensing–Based Hydrocarbon Measurements: A Comparison to FID Measurements"; Journal of Air and Waste Management Assoc. 1996; pp. 46 & 148–158.

Stedman, Donald H.; "Automobile Carbon Monoxide Emissions"; Environmental Science and Technology 1989; vol. 23#2, pp. 147–149.

Adachi, Masayuki, Yamagishi, Yutaka, Inoue Kaori and Ishida, Kozo; "Automotive Emissions Analyses using FTIR Spectrophotometer"; Society of Automotive Engineers 1992; SAE #920723.

Koplow, Michael D., Jimenez, Jose L., Nelson, David D., Schmidt, Stephan E.; "Characterization of On–Road Vehical NO Emissions by Means of a TILDAS Remote Sensing Instrument"; Coordinating Research Council 1997; pp. 8–35 & 9–62.

Guenther, Paul Leonard; "Contributions to On–Road Remoter Sensing of Automobile Exhaust"; University of Denver 1992.

Cox, Frank W., Walls, John R. and Carrel, Mark W.; "Determination of Catalyst Oxidation and Reduction Efficiencies from Tailpipe Emissions Measurements"; Society of Automotive Engineers 1997; SAE #972911.

Lawson, Douglas R., Groblicki, Peter J., Stedman, Donald H., Bishop, Gary A. and Guenther Paul L.; "Emissions from In–Use Motor Vehicles in Los Angeles: A Pilot Study of Remote Sensing and the Inspection and Maintenance Program"; Journal of Air and Waste Management Assoc. 1990; vol. 40#8, pp. 1096–1105.

Stedman, Donald H., Bishop, Gary A. and Pitchford, Marc L.; "Evaluation of a Remote Sensor for Mobile Source CO Emissions"; University of Denver 1991; Rpt.# EPA 600/4–90/032.

McLaren, Scott E., Stedman, Donald H., Greenlaw, Pamela D., Bath, Raymond J., and Spear, Richard D.; "Comparison of an Open Path UV and FTIR Spectrometer"; Air and Waste Management Assoc. 1992; vol. 92–73.10.

Bishop, Gary A., Zhang, Yi, McLaren, Scott E., Guenther, Paul L., Beaton, James E., Stedman, Donald H., Duncan, John W., McArver, Alexander Q., Pierson, William R., Groblicki, Peter J., Knapp, Kenneth T., Zweidinger, Roy B. and Day, Frank J.; Enhancements of Remote Sensing for Vehicle Emissions in Tunnels; Journal of Air and Waste Management 1994; vol. 44, pp. 169–175.

McLaren, Scott E. and Stedman Donald H.; "Flux Measurements Using Simultaneous Long Path Ultraviolet and Infrared Spectroscopy"; Air and Waste Management Assoc. 1990; vol. 90–86.6.

Bishop, Gary A., McLaren, Scott E., Stedman, Donald H., Pierson, William R., Zweidinger, Roy B. and Ray, William D; "Method Comparisons of Vehicle Emissions Measurements in the Fort McHenry and Tuscarora Mountain Tunnels"; Atmospheric Environment 1996; vol. 30#12, pp. 2307–2316.

McLaren, Scott; "Open Path Spectrometers for Atmospheric Monitoring"; University of Denver 1995.

Stedman, Donald H. and Bishop, Gary A.; "An Analysis of On–Road Remote Sensing as a Tool for Automobile Emissions Control"; Illinois Dept. of Energy & Natural Resources 1990; ILENR/RE–AQ–90/05.

Stedman, Donald H., Peterson, James E. and McVey, Iain F.; "On–Road Carbon Monoxide and Hydrocarbon Remote Sensing in the Chicago Area"; Illinois Dept. of Energy & Natural Resources 1991; ILENR/RE–AQ–91/14.

Lyons, Carol E. and Stedman, Donald H.; "Remote Sensing Enhanced Motor Vehicle Emissions Control for Pollution Reduction in the Chicago Metropolitan Area: Siting and Issue Analysis"; Illinois Dept. of Energy & Natural Resources 1991; ILENR/RE–AQ–91/15.

Durbin, Thomas D., Truex, Timothy J. and Norbeck, Joseph M.; "Particulate Measurements and Emissions Characterizations of Alternative Fuel Vehicle Exhaust"; National Renewable Energy Laboratory 1998; NREL/SR–540–25741; Subcont# ACI–7–16637–01.

DiDomenico, John, Johnson, Jim, Webster, Jason and Rendahl, Craig S.; "Preliminary Results from Cold Start Sensor Testing"; Coordinating Research Council 1997; pp. 4–71 & 4–72.

Stephens, Robert D. and Cadle, Steven H.; "Remote Sensing Measurements of Carbon Monoxide Emissions from On–Road Vehicles"; Journal of Air and Waste Management Assoc. 1991; vol. 41#1, pp. 39–46.

Jimenez, Jose L., McRae, Gregory J., Nelson, David D., Zahniser, Mark S. and Kolb, Charles E.; "Remote Sensing of NO and $NO_2$ Emissions from Heavy–Duty Diesel Trucks using Tunable Diode Lasers"; Environmental Science & Technology 2000; pp. 34 & 2380–2387.

Stedman, Donald H., Bishop, Gary A., Guenther, Paul L., Peterson, James E., Beaton, Stuart P. and McVey, Iain F.; "Remote Sensing of On–Road Vehicle Emissions"; University of Denver 1992; Contract #VE–8–1.

Singer, Brett C., Harley, Robert A., Littlejohn, David, Ho, Jerry and Vo, Thu; "Scaling of Infrared Remote Sensor Hydrocarbon Measurements for Motor Vehicle Emission Inventory Calculations"; Environmental Science and Technology 1998; vol. 32#21, pp. 3241–3428.

Atkinson, Chris M., McKain, David L., Gautam, Mridul, El–Gazzar, Laila, Lyons, Donald W. and Clark, Nigel N.; "Speciation of Heavy Duty Diesel Engine Exhaust Emissions"; Coordinating Research Council 1995; pp. 5–71 & 5–92.

Chaney, Lucian W.; "The Remote Measurement of Traffic Generated Carbon Monoxide"; Journal of Air Pollution Control Assoc. 1983; vol. 33#3, pp. 220–222.

Todd, Michael and Barth, Michael; "The Variation of Remote Sensing Emission Measurements with Respect to Vehicle Speed and Acceleration"; Coordinating Research Council 1995; pp. 4–1 & 4–14.

Hoshizaki, H., Wood, A.D and Kemp, D.D.; "Vehicle Inspection Instrumentation"; Lockheed Missiles & Space Company 1973; ARB–3C–235–7.

Sigsby, Jr., John E., Tejada, Silvestre and Ray, William; "Volatile Organic Compound Emissions from 46 In–Use Passenger Cars", Environmental Science & Technology 1987; pp. 21 & 466–475.

* cited by examiner

OPTICAL PATH STRUCTURE FOR OPEN PATH EMISSIONS SENSING

FIELD OF THE INVENTION

The present invention relates generally to remote sensing systems. More particularly, the present invention relates to an apparatus for transmitting, reflecting, and detecting light in an open path sensing system such as a vehicle emission sensing system, having us in detecting and/or measuring one or more components of the air through which the light passes.

BACKGROUND OF THE INVENTION

Current methods of determining whether a vehicle is compliant with emission standards include open path and closed path emissions measurement systems. In a closed path system, an emission sensor is directly connected to the exhaust of the vehicle, such as by insertion into a tailpipe. An open path vehicular emissions measurement system collects data by a means other than a direct connection to the tailpipe, such as a remote sensor that analyzes the individual components of emissions. Open path vehicle emission systems are often preferable to closed path systems because they can be used in numerous locations and do not require the vehicle to stop for testing.

Various open path emission sensing systems have been known. One such device uses a radiation source on one side of a roadway that projects a beam across the roadway to be received by a detector. The radiation source and the detector are located on opposite sides of the roadway. The radiation source emits light spectra that may be used to detect an emission signature by way of absorption of light, or which alternatively may be used to excite emission components so as to cause the components to emit light. The detected emission signature can then be used in various applications, such as the measurement of a vehicle's compliance with emission limits and the determination of the type of fuel that a vehicle is using.

A disadvantage of many known arrangements is that the radiation sources and detectors must be placed on opposite sides of the roadway from each other. Since both the detectors and radiation sources require power to operate, this means that a separate power supply must be provided on each side of the roadway.

Some known arrangements have tried to overcome this problem by using a radiation source on one side of a roadway and a reflective apparatus located on the other side of the roadway.

Accordingly, it is desirable to provide an improved optical transmission, reflection, and detection system as herein disclosed.

SUMMARY OF THE INVENTION

It is therefore a feature and advantage of the present invention to provide an improved optical transmission, reflection, and detection system. In accordance with one embodiment of the present invention, a gas component analysis system includes a first light source capable of emitting at least one beam of light having known emission intensities corresponding to a plurality of infrared, visible, and ultraviolet spectra. The system also includes a reflection unit, a detection unit capable of receiving the beam and measuring received intensities corresponding to the plurality of light spectra, and a processor capable of comparing the emission intensities and the received intensities and identifying a concentration of a component corresponding to the intensities.

Preferably, the system also includes a first off-axis reflector positioned to receive the beam from the first light source and reflect the beam toward the reflection unit. The reflection unit is positioned to receive the beam from the off-axis reflector and reflect the beam. Also preferably, a second off-axis reflector is positioned to direct the beam reflected by the reflection unit so that the beam may be received by the detection unit. Each off-axis reflector preferably comprises a parabolic mirror.

Also preferably, the system also includes a filter wheel positioned to spin about an axis and receive the beam from the first light source and pass the beam to the reflection unit in pulses. The filter wheel preferably includes a plurality of filters, each of which substantially limits the passage of light to a predetermined spectral wavelength or range of wavelengths.

Also preferably, the beam of infrared light travels along an optical path to the reflection unit. In this embodiment, the system also includes a second light source capable of emitting a beam of ultraviolet light, as well as a neutral density filter positioned to direct the beam of ultraviolet light along the optical path to the reflection unit. The neutral density filter should be positioned to direct the beam of infrared light to the reflection unit.

Also preferably, the system also includes a reflector wheel positioned to spin about an axis and receive the beam from the reflection unit and direct infrared components of the beam to the detection unit in pulses.

In accordance with another embodiment, a method of measuring concentrations of one or more components of a gas includes the steps of: (1) emitting at least one beam of light having known emission intensities corresponding to a plurality of infrared, visible, and ultraviolet spectra through the gas; (2) using a reflection unit to reflect the beam; (3) using a detection unit to receive the beam; (4) measuring received intensities in the beam corresponding to the plurality of light spectra; and (5) identifying a concentration of at least one component of the gas corresponding to a ratio of the emission intensities and the received intensities.

Preferably, the method embodiment also includes, before the reflecting step, filtering the beam and passing the beam to the reflection unit in pulses. It may also include, before the detecting step, directing visible and ultraviolet components of the beam and directing infrared components of the beam to the detection unit Also preferably, in the method embodiment the identifying step is performed by a processing device that is programmed to perform the calculation of a component concentration using a formula corresponding to the Beer-Lambert law.

There have thus been outlined, rather broadly, the more important features of the invention in order that the detailed description thereof that follows may be better understood, and in order that the present contribution to the art may be better appreciated. There are, of course, additional features of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION OF PREFERRED EMBODIMENTS OF THE INVENTION

A preferred embodiment of the present invention provides an improved optical transmission, reflection, and detection system for gas component analysis. A preferred embodiment includes a light source unit, which preferably includes an ultraviolet and/or an infrared light source; a reflector unit; and a light detector. Preferably, the light source and detector are included within a single housing. However, the light source and the light detector may optionally be provided in separate housings. The light is transmitted through a gas, such as air containing vehicle emissions, reflected, and detected for analysis and measurement of the amount of absorption that has occurred at known frequencies. The amount of absorption may be used to determine a concentrations of reference gases corresponding to specific frequencies.

Figure 1:
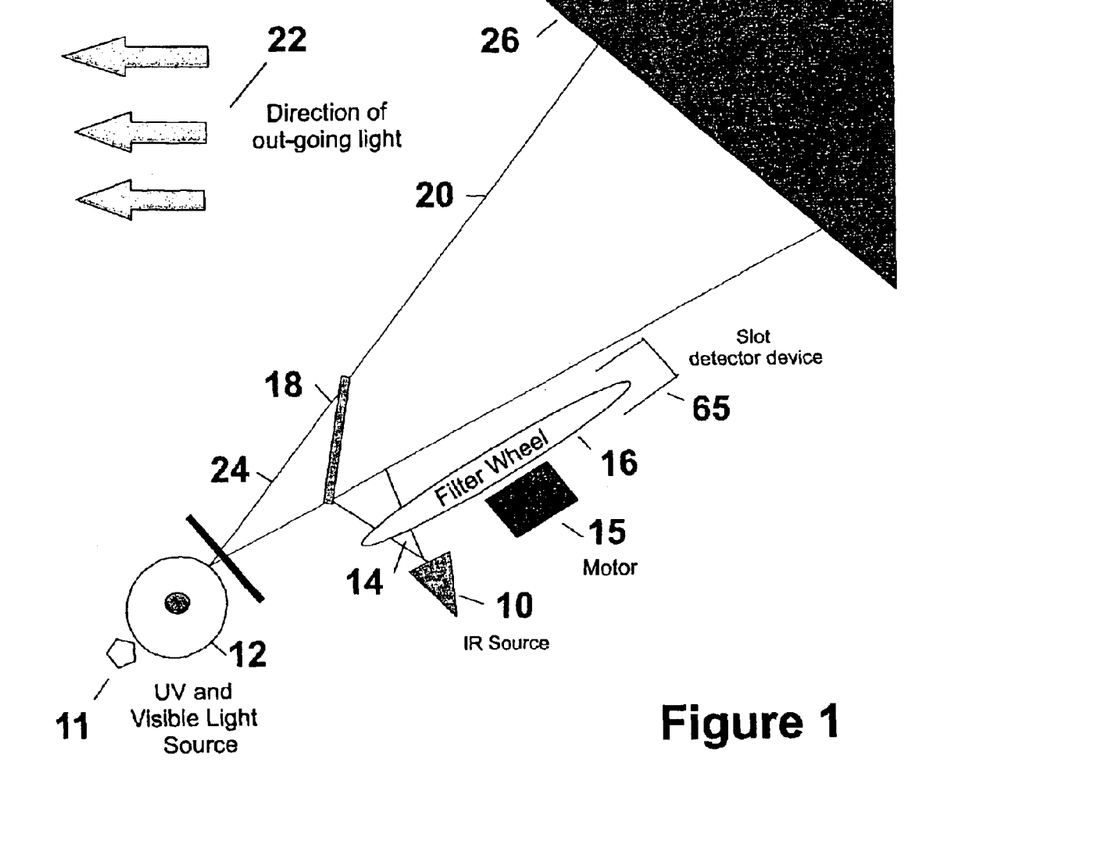
FIG. 1 illustrates a preferred embodiment of a light source component of the present invention.

In a preferred embodiment of this invention, infrared, visible, and ultraviolet radiation are combined into one beam, directed across a path such as a road across which vehicles travel and generate exhaust, reflected back across the path, collected and concentrated, separated again, and analyzed by an one or more detectors and/or spectrometers. The infrared light passes through a sequence of filters, preferably narrow bandpass filters, such that each filter is specific to a gas of interest. In one embodiment, a spinning wheel holds the filters and passes each filter in front of the infrared light source in sequence. In an alternate embodiment, the infrared light is reflected by a spinning reflector, such as a mirror, into a stationary array of filters and elliptical mirrors which focus it directly into an infrared detector A portion of a preferred embodiment of the present inventive apparatus is illustrated in FIG. 1. FIG. 1 illustrates a possible light source component of the present invention. The light source component shown includes an infrared light source 10 and a source or sources of ultraviolet light 12 and/or visible light 11. The infrared light 14 emitted by the infrared source 10 passes through a filter component 16, then it is reflected by a neutral density filter, or beam splitter, component 18 and follows optical path 20 until it reaches an off-axis reflector 26 such as a parabolic mirror. The reflector 26 reflects the infrared light 14 along a path 22 leading to a reflection unit. In addition, ultraviolet and/or visible light 24 that is emitted by the sources 11 and 12 is passed through the neutral density filter 18 such that it also follows optical path 20 to the off-axis reflector 26, where the light is reflected to also follow path 22 toward the reflection unit.

Optionally, only the infrared light source 10, and not the ultraviolet or visible sources, may be provided. In such an embodiment, the neutral density filter 18 may also optionally be omitted with the infrared light source 10 taking the position of the ultraviolet source 12 in such an alternative arrangement.

Preferably, the filter component 16 is a spinning wheel, that is powered by a motor 15 that spins the wheel about an axis. Also preferably, a synchronization device 65 is provided to track the position of the wheel and/or the number or speed of rotations of the wheel.

As FIG. 1 illustrates, where multiple light sources are provided the emitted beams preferably follow the same substantially same optical path toward the reflector 26. The off-axis reflector 26 is positioned such that the angle of incidence formed by incoming and reflected light is an angle other than 180-degree angle. Thus, light transmitted to the reflector 26 is reflected in a direction away from the original light source. Preferably, the focal point is such that the light reflected away from the reflector 26 and the incoming light form an angle of approximately 30 degrees. However, other angles may be provided in alternate embodiments. In addition, the neutral density filter component 18 preferably is designed so that it substantially reflects infrared light but substantially passes ultraviolet, although 100% reflection/detection of such light components is not required. Also preferably, the off-axis reflector is protected by a calcium fluoride ($CaF_2$) window or cover.

The infrared light source item 10 preferably is a low power consumption (preferably less than about ten watts) integrating sphere comprised of a filament positioned around a central member. The filament and member, when energized, emit light, and the sphere, with most or all of its internal surface comprised of reflective material, concentrates the light to exit through an opening in the sphere, thus creating a pure source of infrared light. Preferably, the light source has little or no cool spots from filament or other material that would interfere with a homogenous transmittance of light. However, other light sources, such as pure bulbs or filaments, may be used.

The visible light source 11 is preferably a light emitting diode (LED) or other visible source, and the ultraviolet light source 12 is preferably an ultraviolet lamp such as deuterium lamp, a xenon lamp, or another lamp that provides ultraviolet light in spectra of interest. The visible light source 11 is focused through an orifice in the ultraviolet lamp, combining the visible and ultraviolet light (UV/VIS). The filter/mirror 18 preferably is a neutral density filter positioned at an angle to the axis of the beam of UV/VIS light. The neutral density filter 18 acts as a beam combiner, reflecting the light from the infrared source 10 and allowing the UV/VIS light to pass through. The off-axis reflector 26 then collimates the combined light and directs it across the path 22.

Figure 2:
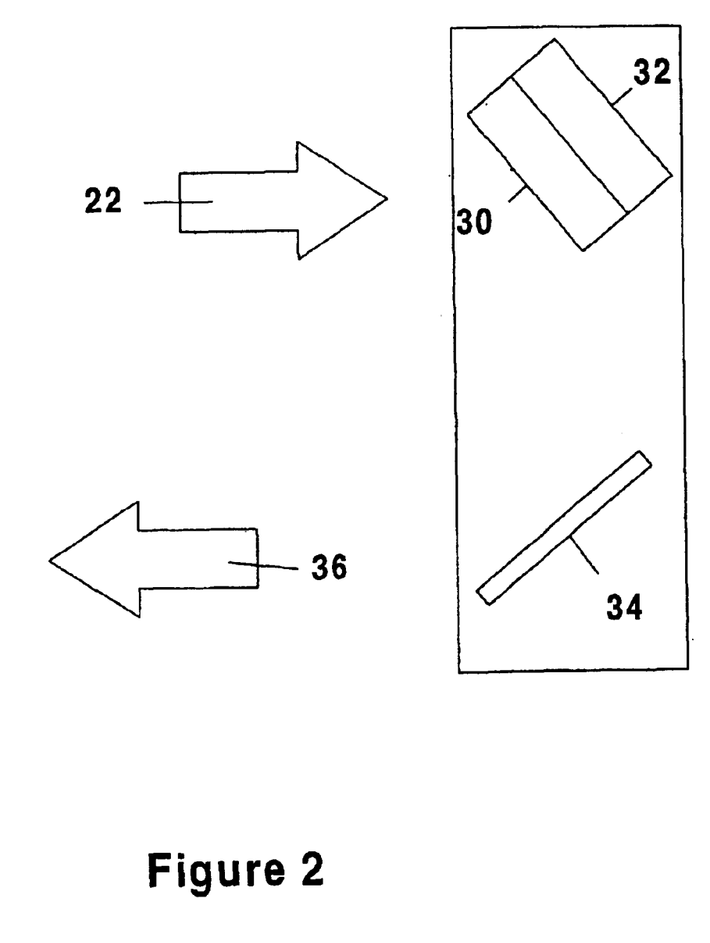
FIG. 2 illustrates a preferred embodiment of a reflective element of the present invention.

FIG. 2 illustrates an exemplary reflection unit, which in an embodiment used to detect vehicle emissions is preferably placed across the road from the light source component. The reflection unit includes a retro-reflective system, preferably a vertical system and preferably comprising at least three mirrors positioned to form 90 degree angles with respect to each other. Referring to FIG. 2, incoming light 22 is reflected by a first mirror 30 and a second mirror 32. The first and second mirror are adjacent or substantially adjacent to each other to form a 90 degree angle. The light reflected by the first and second mirrors is transmitted to a third mirror 34, which is positioned to be at an approximately 90 degree angle from the first mirror 30 and second mirror 32. FIG. 2 illustrates the first mirror 30 along its flat reflective portion, and the second mirror 32 along its edge so that the flat reflective portions of each of the first mirror 30 and second mirror 32 form a 90 degree angle. FIG. 2 illustrates the edge of third mirror 34 such that the flat reflective portion of third mirror 34 forms a 90 degree angle with the flat reflective portions of both first mirror 30 and second mirror 32. Light 36 that is reflected by third mirror 34 is then transmitted to the detection unit. Preferably, the angles described above are perfect 90 degree angles, although minor discrepancies may be allowed. The incoming light 22 and/or the reflected light 36 pass through an air component that is to be measured, such as vehicle emissions.

Figure 3:
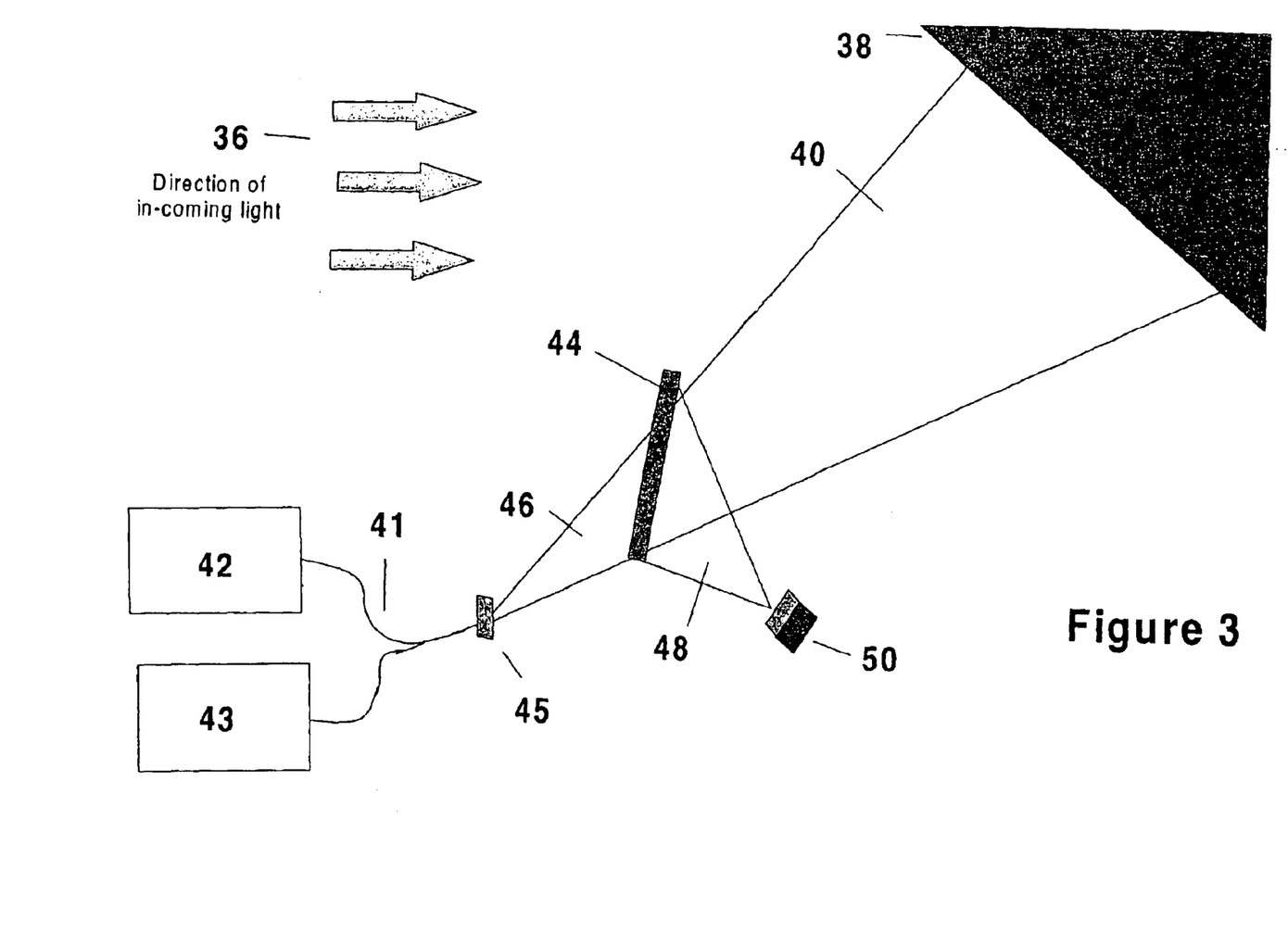
FIG. 3 illustrates a preferred embodiment of a detector component of the present invention.

FIG. 3 illustrates an exemplary detector component that receives light transmitted by the source component of FIG. 1, and passing light generated by the source component of FIG. 1 to the reflective system of FIG. 2. Referring to FIG. 3, incoming light 36 is reflected by an off-axis reflector 38 such as a parabolic mirror that reflects light along an optical path 40 to form an angle other than a 180 degree angle with the incoming light 36. The light transmitted along optical path 40 is reflected by a beam splitter or filter 44, preferably a neutral density filter, that directs infrared light 48 toward infrared detector 50. Preferably, the infrared detector 50 is positioned slightly off the focal point so that the light can over-bathe the detector's active area to allow for system vibration without adversely affecting measurement accuracy. The infrared detector 50 can be a lead-selenide, mercury-cadmium-telluride, or another suitable infrared detector, preferably having multistage thermal electric cooling.

Figure 5:
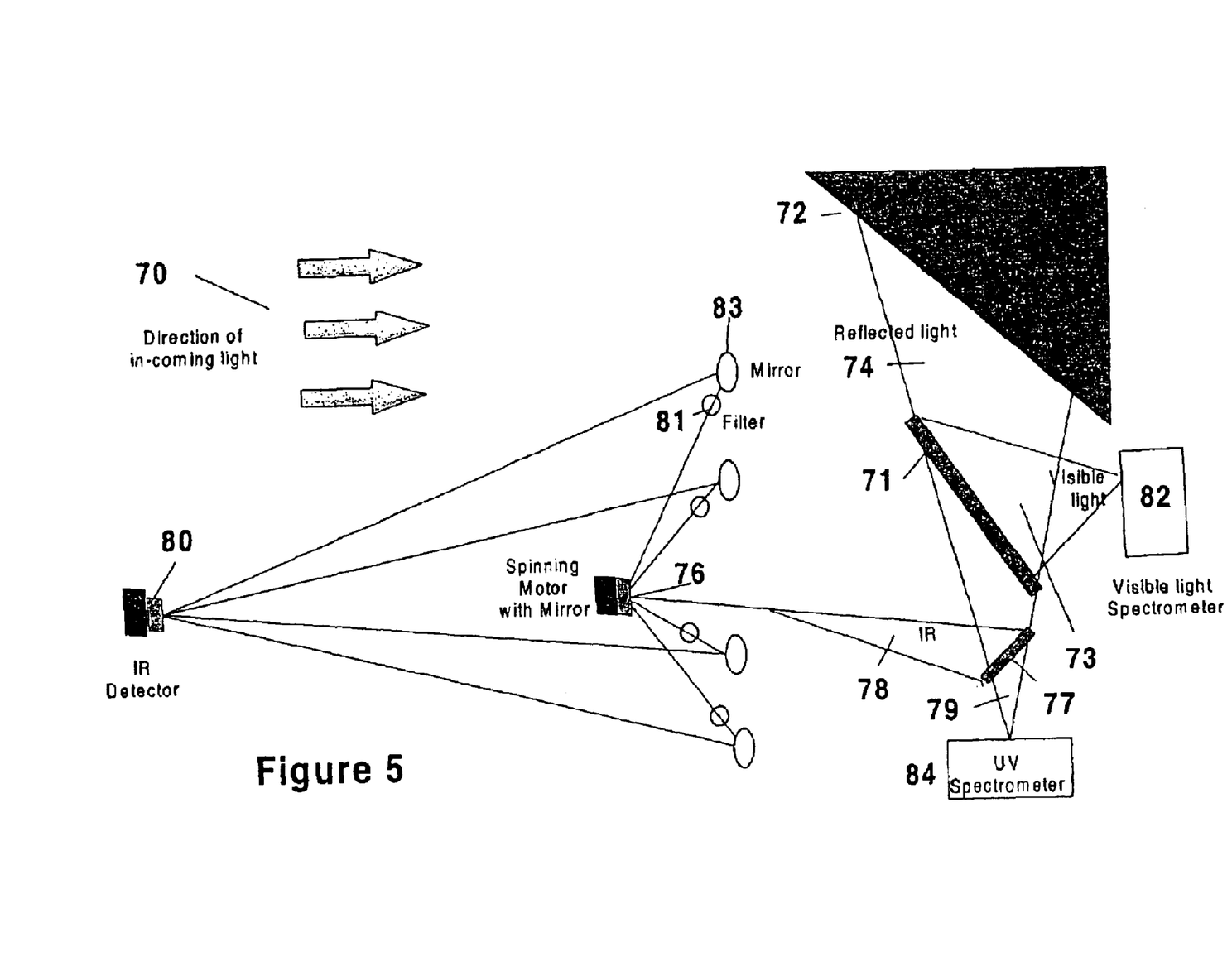
FIG. 5 illustrates an alternate embodiment of a detector component of the present invention.

The neutral density filter 44 passes all or portions of visible and/or ultraviolet light 46 so that the visible and ultraviolet spectra may be measured by one or more spectrometers 42 and 43. The beam splitter or filter 44 may comprise any reflective or transmissive device, such a neutral density filter, that allows different wavelengths of light to be passed and/or reflected. The UV/VIS light which passes through the filter 44 is split off and carried to the respective spectrometers in one of two ways. The first is to focus it on the end 45 of a Y-shaped split optical fiber cable that sends a portion of the light to each spectrometer. The second is to use a third beam splitter to focus a portion of the light into the visible spectrometer 82 and the other portion into the UV spectrometer 84 (either with or without optical fiber cables) as illustrated in FIG. 5. In either case, the light can be slightly defocused or overbathe the light orifice of the spectrometer for resistance to vibration and coincident reduction of light with the vibration. Preferably, referring again to FIG. 3, the path 46 along which ultraviolet and/or infrared light is passed comprises one or more cables that pass the light directly to the one or more spectrometers 42 and 43.

The infrared detector 50 detects the intensity of light along various spectra. The spectra considered correspond to various known components of vehicle exhaust gases. For example, the detector may detect the intensity of light along the following spectra for a measurement of the following vehicle emission components:

| Component | Wavelength |
|---|---|
| Carbon Monoxide (CO) | 4.65 $\mu$ |
| Carbon Dioxide (CO$_2$) | 4.30 $\mu$ |
| HC$_1$ | 3.45 $\mu$ |
| HC$_2$ | 3.17 $\mu$ |
| HC$_3$ | 3.01 $\mu$ |
| HC$_4$ | 3.31 $\mu$ |
| H$_2$O | 2.75 $\mu$ |
| Reference | 3.85 $\mu$ |

Other wavelengths corresponding to other components, as well as fewer than all of the above-listed wavelengths, may be measured.

Using a processing device, the intensities measured by the detector at each desired wavelength are compared to intensities of light emitted by the source at a reference wavelength using a test to measure the amount of the component associated with the wavelength that was detected in the sample of open air.

Preferably, concentrations of gases may be derived using the Beer-Lambert Law $L_N(I/I_o)=L$ where LC is the concentration of the component being measured. However, other tests and formulae may be used in alternate embodiments.

The Beer-Lambert Law relates absorbance to concentration where an amount of change [dI(v)] in light intensity [I(v)] at a wavelength=$\lambda$ is proportional to the concentration of species [c(v,y)] that can absorb frequency=v and may vary in space across the beam in the y direction:

$$dI(v)/I(v)=kc(v,y)dy$$

When this equation is integrated, it becomes:

$$ln(I/I_o)=k[(\text{Intregral})c(v,y)dy]$$

Where I is the intensity of the sample light; $I_o$ is the intensity of the reference beam; k is a constant that depends upon the temperature, pressure and molecular structure and; c is the concentration.

If the concentration of a pollutant is uniformly distributed along the path length L and the atmosphere has only one absorbing species, then the equation becomes:

$$ln(I)/I_o=-kcL$$

where I is the source light intensity, $I_o$ is the detected light intensity, and kcL is the concentration of the component being measured. When the atmosphere has more than one absorbing species and the path length is not uniform, then the equation can be written as:

$$ln(I)/I_o=\Sigma_i-k_i(v_1)\Sigma c_i(v,y)dy$$

where i species are mixed in the plume with varying concentrations $c_i$ across the plume's width y. The instrument preferably uses a spectral library and this equation to calculate the absorbance and concentration of each species.

Using combustion equations enables the simplified equation ln (I)/$I_o$=−kcL to be applied to the remote sensing device, even though the tailpipe plume may not be evenly distributed across a traffic lane. The combustion equations may be used to calculate pollutant concentrations in the undiluted exhaust with the ratios of the pollutants to carbon dioxide.

Figure 4:
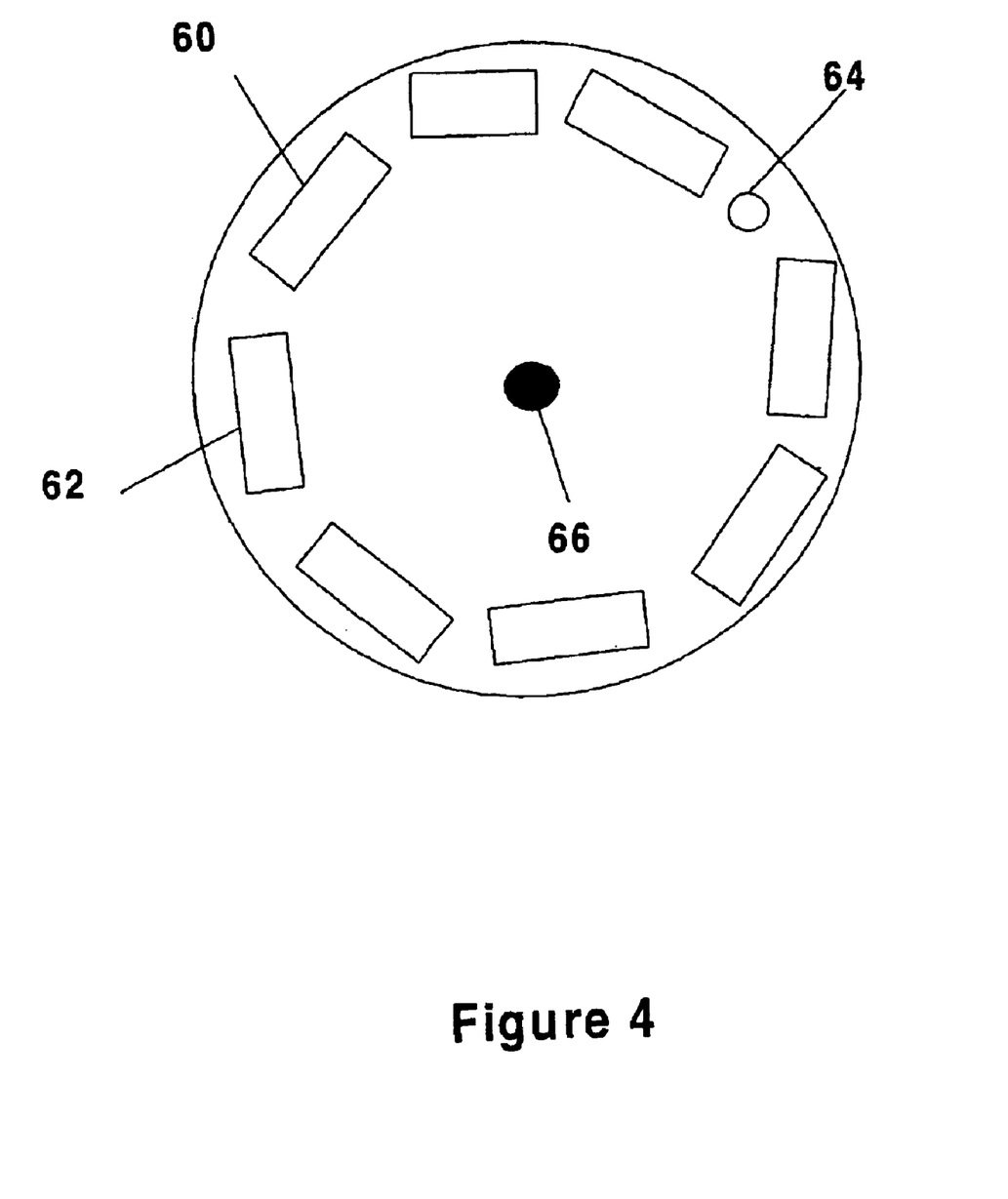
FIG. 4 illustrates an exemplary spectral wheel that may be used in accordance with one embodiment of the present invention.

In a preferred embodiment, the transmission and detection of light at the wavelengths of mid-infrared listed above is accomplished by using a spinning filter wheel as the filter component (referred to in FIG. 1 as item 16). FIG. 4 illustrates an exemplary spinning filter wheel. Referring to FIG. 4, the spinning filter wheel contains light filters such as 60 and 62 that correspond to wavelengths associated with individual emission components, such as those illustrated in the above chart. The illustration in FIG. 4 illustrates a wheel having eight filters, thus corresponding to the wavelengths and emission components listed in the chart set forth above. However, fewer and/or additional filters, corresponding to fewer and/or additional emission components, may be used in alternate embodiments. Each filter is designed to only allow light of a specific wavelength or wavelength range to pass through it.

In addition, the filter wheel preferably will have one or more synchronization marks such as 64 that, when detected by a synchronization unit (illustrated in FIG. 1 as item 65), may be used to define either the exact filter or the start of a set of filters that will be in the optical path. The wheel may have one or more opaque areas either between every filter or only between specific filters. The opaque areas prohibit source light from getting to the detector when the opaque area passes over the infrared source. In operation, the wheel spins about an axis 66 at high speeds, preferably up to 20,000 rotations per minute, up to 30,000 rotations per minute, or more, to form a pulse train of infrared light. The known speed allows the detector to determine, based on the pulse, the wavelength of light that should be compared, so that appropriate concentrations can be measured. This combination overcomes disadvantages of prior art, which require discrete detectors for each wavelength.

The UV/VIS light source illustrated in FIG. 1 as item 11 is an option and is not required. However, such a source allows the performance of additional tests on detected light associated with visible and ultraviolet spectra, such as an opacity test. One type of opacity test that may be performed is the Society of Automotive Engineers J1667 opacity test, also known as the snap acceleration test, which measures concentrations of light spectra in ranges such as 562 through 568 nanometers. Preferably, the visible portion of UV/VIS source 11 can also permit detection of blue smoke, which may be indicative of a vehicle that is burning excessive lubricating oil.

In accordance with an alternate embodiment of the present invention, the light source unit illustrated in FIG. 1 may omit the filter component 16 such as the spinning filter wheel. In accordance with this embodiment, an alternate detector unit is provided. FIG. 5 illustrates such a detector unit. Referring to FIG. 5, incoming light 70 that is transmitted by the source unit through an emission to be analyzed is reflected by an off-axis reflector 72, which focuses a light beam 74 onto a first neutral density filter 71 that directs visible light 73 to a visible light spectrometer 82. Remaining components of the light are focused on a second neutral density filter 77 that focuses reflected light 79 to an ultraviolet spectrometer 84 and reflects light 78 to a rotating mirror 76. Each neutral density filter directs ultraviolet or visible components of the light stream to a corresponding spectrometer 82 or 84, preferably via cables or optical fibers, but optionally by direct focus. The rotating mirror 76 preferably is similar to the spinning filter wheel of FIG. 4, except that instead of a rotating mass containing filters, the rotating mass is a single-faceted mirror. The rotating mirror 76 directs infrared light 78 one or more bandpass filters such as 81 that filter the individual spectra and direct the filtered light to corresponding elliptical focusing mirrors 83 that direct light to an infrared detector 80 which may be used to detect individual components of the light. The rotating mirror 76 preferably spins at a speed of up to 60,000 rotations per minute or more, although other speeds may be used.

Figure 6:
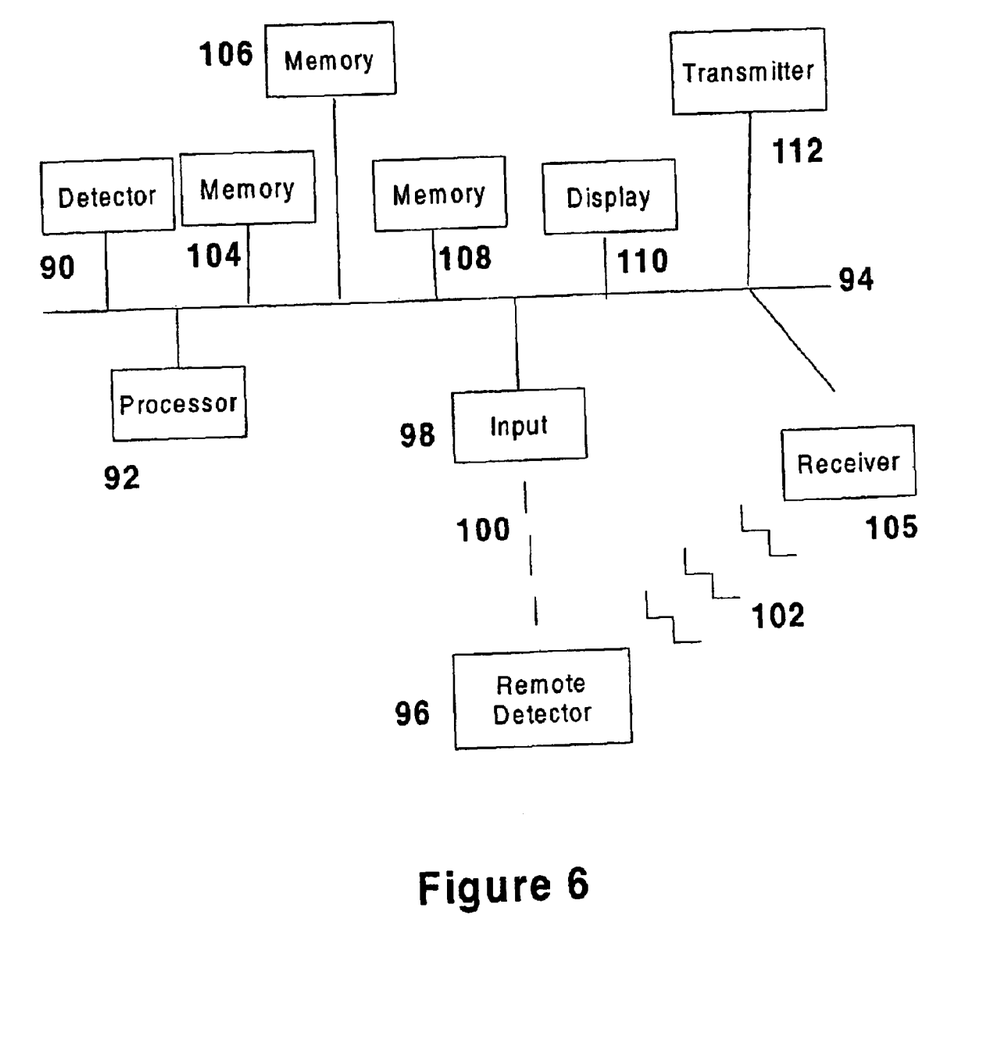
FIG. 6 illustrates several elements of an exemplary computer of a type suitable for carrying out certain functions of the present invention.

FIG. 6 illustrates several elements of a computer processing device that may be used in accordance with a preferred embodiment of the present invention. Referring to FIG. 6, the detector 90 delivers emissions-related data to a processor 92. The detector may be any of the detectors or spectrometers as illustrated in FIGS. 3 and 5, or any device that receives or contains information collected by such detectors or spectrometers. In the embodiment illustrated in FIG. 6, the detector 90 is part of the unit that contains the processor 92, and the delivery is performed by a direct link such as a serial bus 94. However, the processor 92 and detector 90 may be separate, such as with the remote detector 96 illustrated in FIG. 6. Where a remote detector is used, the data may be delivered to the processor 92 by a communications link 100 that delivers the data to an input port 98 such as a communications port. An optional wireless communications link 102 and receiver 105 for such a wireless communication are also illustrated in FIG. 6. The communications link 102 may be a direct wire, a wireless communications link, a global communications network such as the internet, or any other communications medium The system illustrated in FIG. 6 also includes a memory 104 which may be a memory such as a hard drive, random access memory and/or read only memory. Other memory devices 106 and 108 such as a CD-ROM, CD-R, DVD, floppy drive, ZIP drive, microdrive, compact flash, or other memory device may also be included. The device also optionally and preferably includes a display 110 and/or a transmitter 112 for providing output to a user or another device.

The many features and advantages of the invention are apparent from the detailed specification, and thus, it is intended by the appended claims to cover all such features and advantages of the invention which fall within the true spirits and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A gas component analysis system, comprising:

a first light source that emits at least one beam of light having known emission intensities corresponding to a plurality of infrared, visible, or ultraviolet spectra;

a reflection unit;

a filter wheel positioned to spin about an axis and receive the beam from the first light source and pass the beam to the reflection unit in pulses;

a detection unit that receives the beam and measures received intensities corresponding to the plurality of light spectra;

a reflector wheel positioned to spin about an axis and receive the beam from the reflection unit and direct infrared components of the beam to the detection unit in pulses; and a processor that compares the emission intensities and the received intensities and identifies a concentration of a component corresponding to the intensities.

2. The system of claim 1 further comprising:
   a first off-axis reflector positioned to receive the beam from the first light source and reflect the beam toward the reflection unit, wherein the reflection unit is positioned to receive the beam from the off-axis reflector and reflect the beam; and
   a second off-axis reflector positioned to direct the beam reflected by the reflection unit to be received by the detection unit.

3. The system of claim 2 wherein each off-axis reflector comprises a parabolic mirror.

4. The system of claim 1 wherein the filter wheel includes a plurality of filters, each of which substantially limits the passage of light to a predetermined spectral wavelength or range of wavelengths.

5. The system of claim 1 wherein the beam of infrared light travels along an optical path to the reflection unit, and further comprising:
   a second light source capable of emitting a beam of ultraviolet light;
   a neutral density filter positioned to direct the beam of ultraviolet light along the optical path to the reflection unit.

6. The system of claim 5 wherein the neutral density filter is further positioned to direct the beam of infrared light to the reflection unit.

7. The system of claim 1 wherein the first light source comprises an integrating sphere.

8. The system of claim 1 wherein the reflection unit comprises a vertical retro-reflective unit that includes at least three mirrors.

9. The system of claim 1 wherein the first light source and the reflection unit are positioned so that the beam passes through a medium to be analyzed before reaching the reflection unit.

10. The system of claim 1 wherein the reflection unit and the detection unit are positioned so that the beam passes through a medium to be analyzed before reaching the detection unit.

11. The system of claim 1 wherein the detection unit comprises at least one of an infrared detector and one or more spectrometers capable of measuring received intensities corresponding to a plurality of non-infrared spectra.

12. A method of measuring concentrations of one or more components of a gas, comprising the steps of:
   emitting at least one beam of light having known emission intensities corresponding to a plurality of infrared, visible or ultraviolet spectra through the gas;
   reflecting the beam, using a reflection unit;
   before the reflecting step, filtering the beam and passing the beam to the reflection unit in pulses;
   reflecting the beam off of a reflector wheel positioned to spin about an axis and receive the beam from the reflection unit;
   receiving the beam from the reflector wheel, using a detection unit;
   measuring received intensities in the beam corresponding to the plurality of light spectra; and
   identifying a concentration of at least one component of the gas corresponding to a ratio of the emission intensities and the received intensities.

13. The method of claim 12 further comprising, before the detecting step, directing visible and ultraviolet components of the beam and directing infrared components of the beam to the detection unit.

14. The method of claim 12 wherein the identifying step is performed by a processing device that is programmed to perform the calculation of a component concentration using a formula corresponding to the Beer-Lambert law.

15. A gas component analysis system, comprising:
   a means for emitting a first beam of infrared light having known emission intensities corresponding to a plurality of infrared spectra;
   a means for filtering the first beam into a plurality of pulsed spectral components;
   a means for reflecting the first beam;
   a means for reflecting the first beam off of a reflector wheel positioned to spin about on axis and receive the beam from the reflection means;
   a means for receiving the first beam from the means for reflecting;
   a means for measuring received intensities corresponding to the plurality of infrared spectra; and
   a means for identifying a concentration of a component corresponding to the received intensities.

16. The system of claim 15 further comprising:
   a means for emitting a second beam of ultraviolet light corresponding to a plurality of ultraviolet spectra;
   a means for reflecting the second beam;
   a means for receiving the second beam; and
   a means for measuring received intensities corresponding to the plurality of ultraviolet spectra.

17. The system of claim 15 further comprising:
   a means for emitting a third beam of light corresponding to the plurality of visible spectra;
   a means for reflecting the third beam; and
   a means for measuring received intensities corresponding to the plurality of visible spectra.

* * * * *